United States Patent [19]

Colombo et al.

[11] 4,220,861

[45] Sep. 2, 1980

[54] GAMMA CAMERA TOMOGRAPHY APPARATUS

[75] Inventors: Sergio Colombo; Luigi Terra, both of Milan, Italy

[73] Assignee: SELO Societa Electtronica Lombarda S.p.A., Milan, Italy

[21] Appl. No.: 898,038

[22] Filed: Apr. 20, 1978

[30] Foreign Application Priority Data

Jun. 15, 1977 [IT] Italy ............................ 24713 A/77

[51] Int. Cl.² ........................... G01T 1/20; G12B 9/00
[52] U.S. Cl. .................................. 250/363 S; 250/521
[58] Field of Search ................. 250/363 S, 445 T, 521

[56] References Cited

U.S. PATENT DOCUMENTS

| | | | |
|---|---|---|---|
| 3,870,886 | 3/1975 | Casale | 250/363 S |
| 3,983,399 | 9/1976 | Cox, Jr. et al. | 250/363 S |
| 4,057,726 | 11/1977 | Jaszczak | 250/363 S |
| 4,131,802 | 12/1978 | Braden et al. | 250/363 S |

Primary Examiner—Alfred E. Smith
Assistant Examiner—Janice A. Howell
Attorney, Agent, or Firm—Shlesinger, Fitzsimmons & Shlesinger

[57] ABSTRACT

This invention relates to a gamma camera tomography apparatus. According to the invention, an apparatus for making tomographic or normal surveys by means of a gamma camera comprises a base frame, which rotatably supports a discoidal member of horizontal axis, on which an articulation support for a survey head containing a gamma camera is radially mobile.

Said discoidal member comprises a central hole, through which the body of a patient supported on a sliding bed is able to pass. There are provided motor means for rotating the discoidal member for radially moving the head support.

10 Claims, 6 Drawing Figures

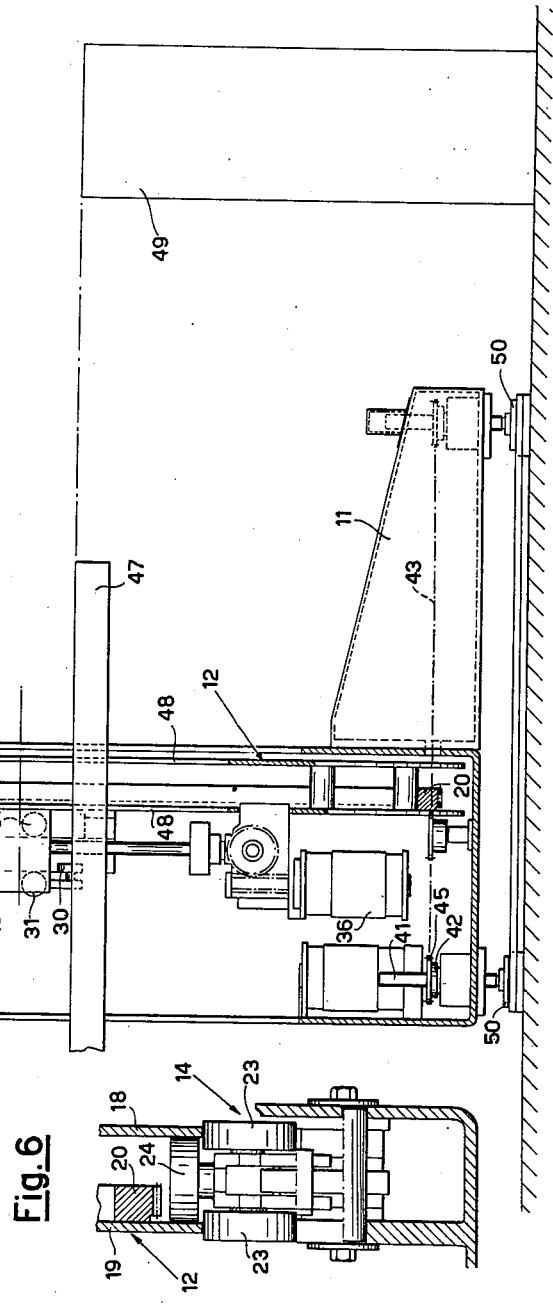
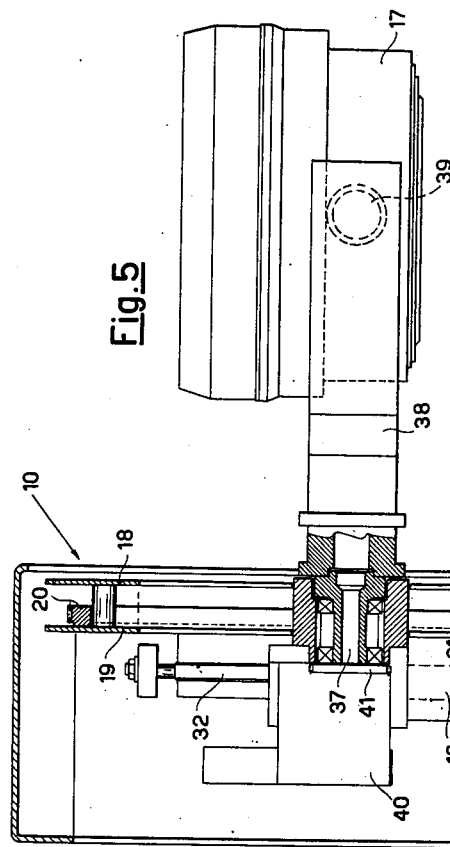
Fig.5
Fig.6

GAMMA CAMERA TOMOGRAPHY APPARATUS

This invention relates to a gamma camera tomography apparatus.

The construction of such an apparatus involves problems which are not easily solved, in that a structure must be provided which is able to support a gamma camera in a manner mobile along a circumference about a patient, so as to take radial views thereof. In order to make the apparatus of universal use, i.e. also able to survey images by the usual method with the gamma camera stationary, the survey head must be able to move about central axes which are orthogonal to each other.

These kinematic requirements, which are already complicated, are aggrevated by the fact that the survey head is of considerable weight, and in addition has to be suspended above a patient, and must thus obviously be safe. In addition, the movements must be made with considerable accuracy.

These requirements have been satisfied by the apparatus according to the invention, comprising a base frame which at its periphery rotatably supports a discoidal member of horizontal axis on which an articulated support for a survey head is radially mobile, the discoidal member comprising a central hole through which the body of a patient supported on a sliding bed can pass, there being provided motor means for rotating the discoidal member and for radially moving the head support.

Further constructional details will be more evident from the description given hereinafter by way of example of one embodiment of the apparatus according to the invention, shown on the accompanying drawings in which:

FIGS. 2, 3, 4 and 5 are sections on the lines II—II, III—III, IV—IV and V—V respectively of FIG. 1;

FIG. 6 is a sectional view of a detail on the line VI—VI of FIG. 1.

Figure 1:
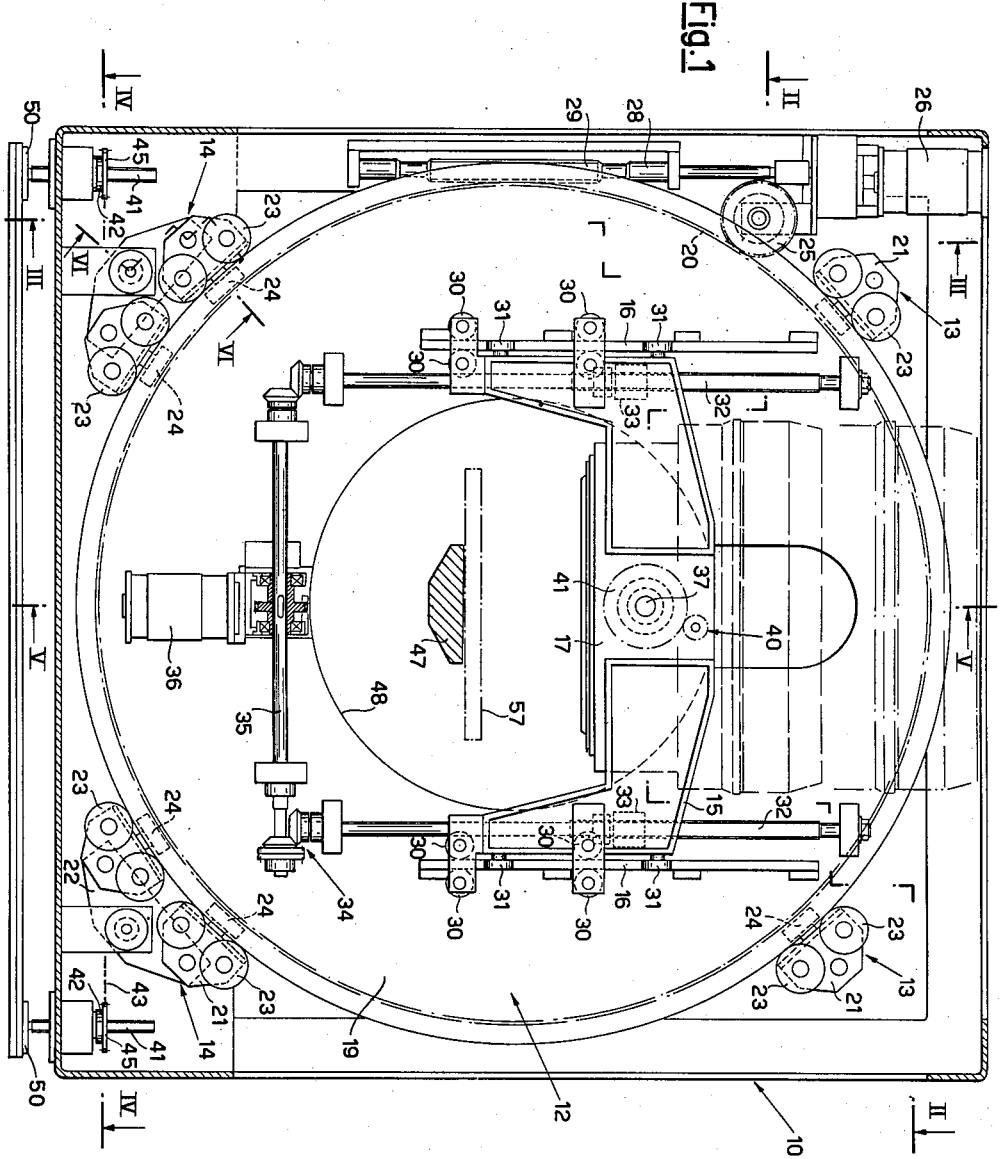
FIG. 1 is a rear view of the apparatus.
Figure 2:
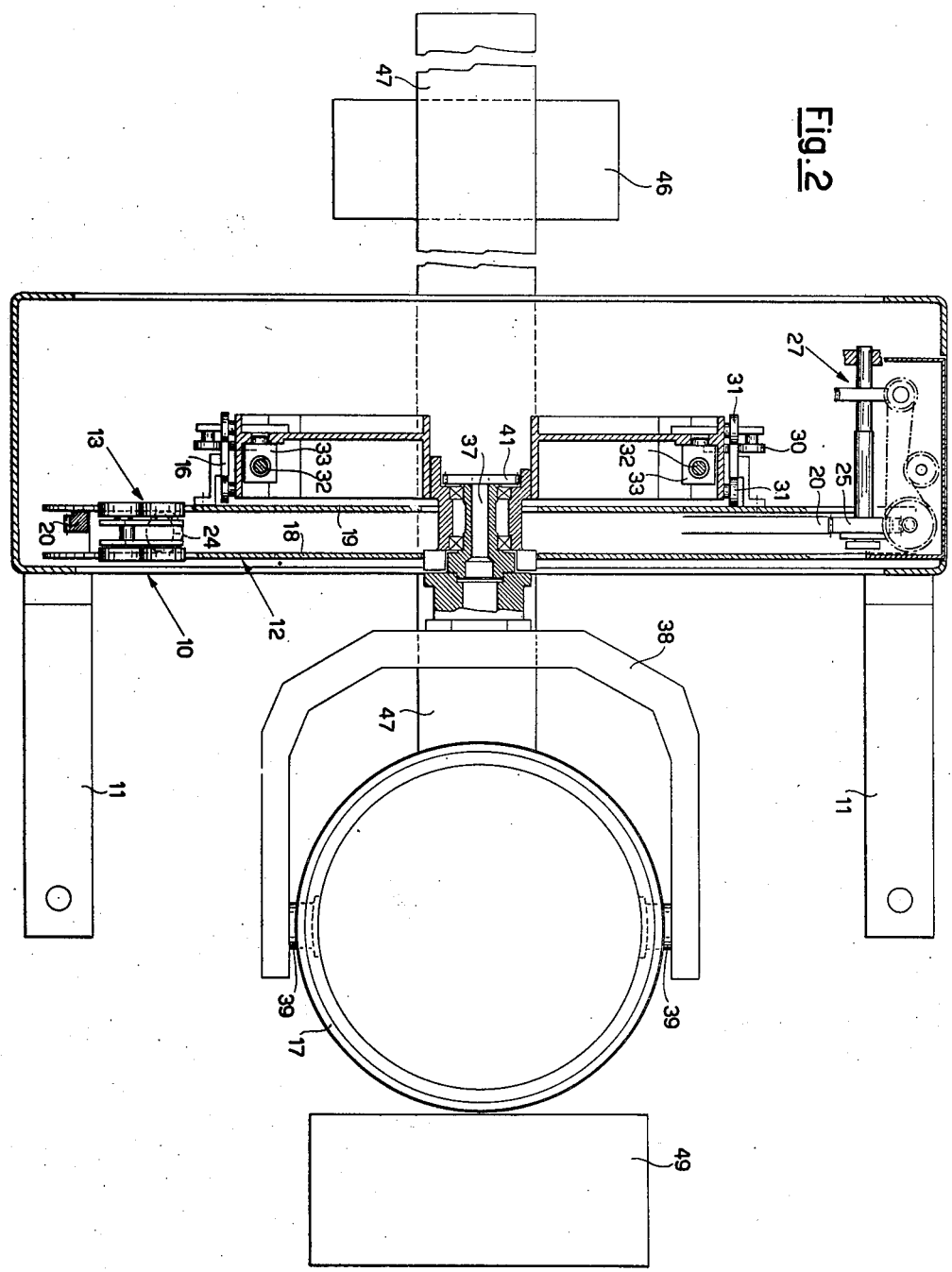
Figure 3:
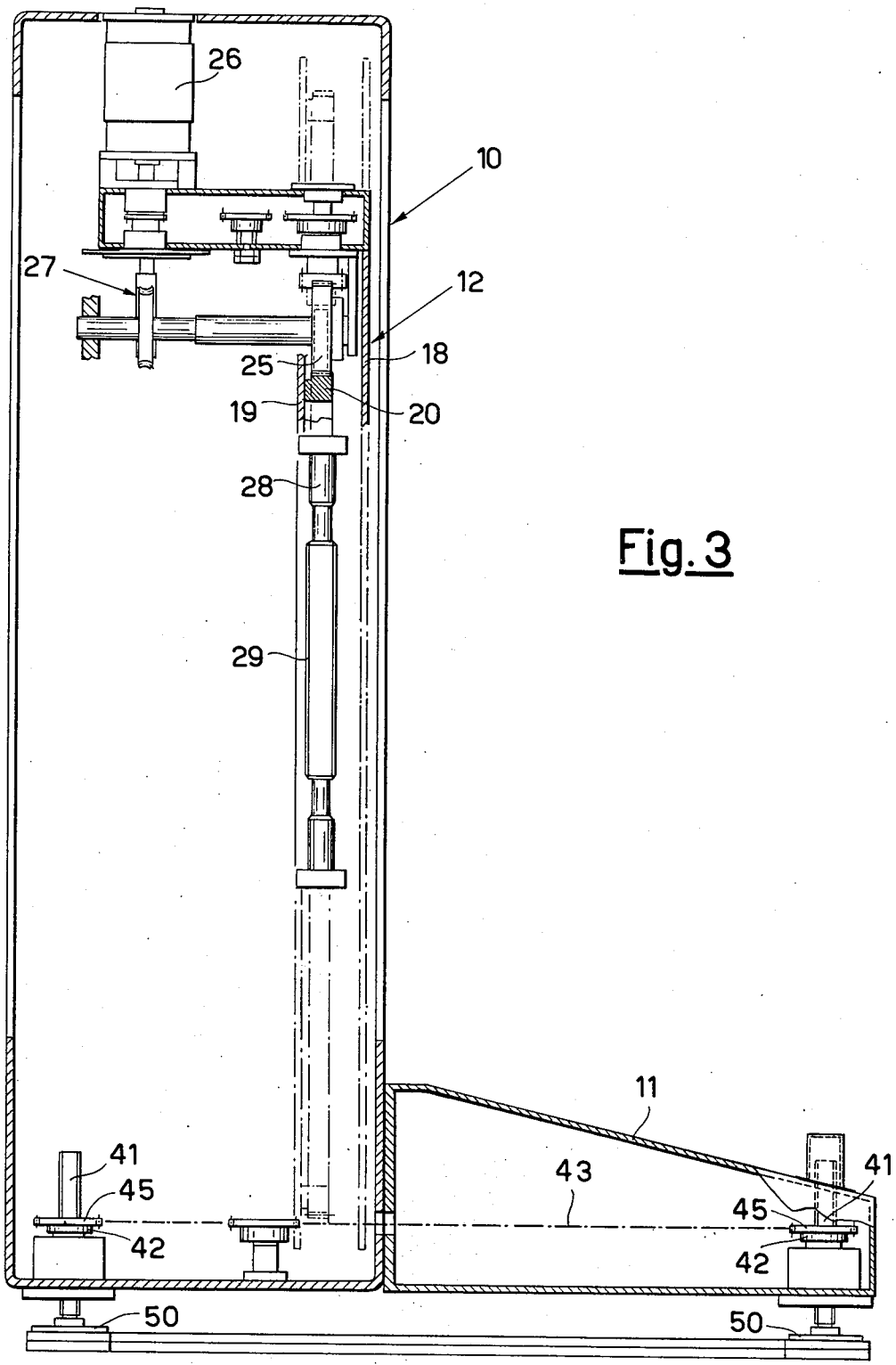
Figure 4:
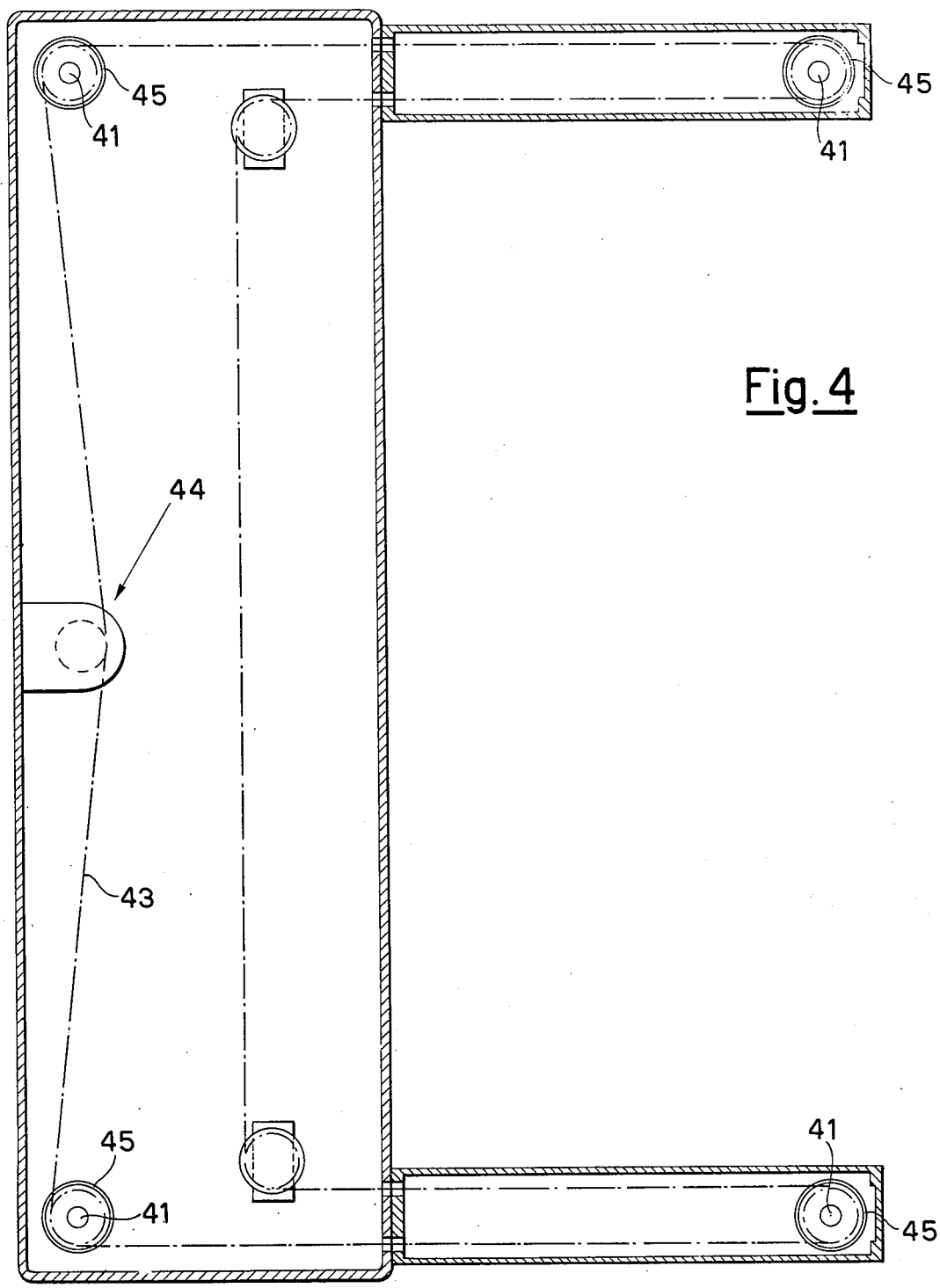

As shown on the drawings, the apparatus comprises a frame 10 provided with two projecting legs 11.

A discoidal member 12 moves within the frame, and is guided by lower supports 14 and upper supports 13.

On the member 12 there is mounted a support 15 which slides radially along guides 16 and supports the survey head 17.

The discoidal member 12 is formed from two facing discs 18 and 19 between which is disposed a ring gear 20. The supports 14 are formed from two carriages 21 supported to swivel on the frame by a rocker arm 22. Each carriage comprises two pairs of idle wheels 23 which roll on the surface of the discs 18 and 19, and a central idle wheel 24 which guides the discs axially. The upper supports 13 are analogous to the supports 14, and comprise only one carriage each because of the smaller force which they are required to support.

The member 12 is moved by a pinion 25, which is driven by the motor 26 via a worm-gear drive 27 and engages in the ring gear 20. The motor shaft transmits motion by a chain to the shaft 28 which carries the worm 29, which also engages in the ring gear 20. The number of teeth on the pinion 25 and worm 29 and the ratio of their rotational speeds are such that both tend to impose the same peripheral speed on the ring gear 20.

One of the two elements, preferably the worm 29, engages in the ring gear with a large degree of slack so as to prevent contact between the toothing in practice. Any force required for the rotation is therefore transmitted in actual fact by the pinion 25. The sole purpose of the worm 29 is therefore that of a safety retainer by virtue of the irreversibility of the worm-ring gear transmission, should the force transmission by the pinion 25 be interrupted for any reason. Because the worm 29 does not operate on the ring gear 20 under normal conditions, the engagement between these two parts can therefore be very approximate, it being necessary only to provide sufficient interference to retain the ring gear 20 when abandoned by the kinematic linkage which terminates at the pinion.

The support 15 slides on guides 16 via pairs of idle rollers 30 and 31 of orthogonal axes. The movement radial to the member 12 along the guides is provided by worms 32 supported on the disc 19 and engaging in nut screws 33 on the support 15.

The worms 32 are driven, by way of bevel gear pairs 34, by a shaft 39 driven by the geared motor 36.

A fork 38 is pivoted at 37 to the support 15 and carries the actual head 17 pivoted at 39. The fork is rotated about the axis of the pivot 37 by a geared motor indicated diagrammatically at 40, which by way of a pinion engages with a gear 41 mounted on the pivot 37.

A similar servomechanism rotates the head about the pivots 39. These servomechanisms are of known type generally used for moving survey heads in conventional apparatus in which the support 15 is replaced by a fixed support, and will therefore not be described in detail.

On the base of the frame 10 at the ends of the legs 11 there are mounted feet 50 with a screwed shank 41 which engages in a nut screw 42 rotatably coupled to the structure of the frame and legs respectively. A chain 43, driven by a geared motor 44, winds about all the sprockets 45 rigid with the nut screws 42.

Thus by operating the geared motor 44, the threaded shanks can be made to emerge in an adjustable manner, so raising or lowering the entire structure of the apparatus at will.

The apparatus is completed by a floor support 46 which supports a beam 47 extending through the central hole 48 in the discs 18 and 19, and by a further support 49. A patient's bed 57, shown by a dashed and dotted line in FIG. 1, can then be disposed between the support 49 and the end of the projecting beam 47, and then slid along the beam so that each cross-section of the patient reaches a position corresponding with the head 17. Between the head and the bed there can be provided means for guiding and controlling the longitudinal displacement of the bed, which are not shown, to facilitate or automate its movements.

The facility for making surveys by means of the described apparatus, and its versatility, will be readily apparent to the expert.

By moving the chain 43, the apparatus is moved until the axis of the hole 48, i.e. the axis of revolution of the head 17, is suitably disposed relative to the patient on the bed 57. By operating the motor 36, the radius of revolution of the head 17 is suitably adjusted, this being attained by rotation of the discoidal member 12. The worm 29 represents a satisfactory safety device, even when the head is disposed on a horizontal diameter of the member 12, thus causing a maximum moment to act on the member, this moment being able to reach a very high value because of the large weight of the head.

The large radius of the discs 18 and 19, and the perimetral arrangement of the supports 13 and 14, enable the considerable masses concerned to be guided correctly and smoothly, thus allowing the tomography to be correctly carried out.

It should be noted that by simply withdrawing the support 49 and halting the unit 12 in a predetermined angular position, the apparatus can perform the function of the normal gamma camera apparatus in which the patient is disposed in any suitable position, for example orthogonally to the axis of the discoidal unit 12. The cantilever mounting of the head 17 is advantageous for this purpose, in that as the head is supported by the fork 38 in an automatically mobile manner, it can be disposed on the vertical over the patient lying in a conventional bed.

The aforegoing structure is described by way of example only, and numerous modifications can be made thereto without leaving the scope of the inventive idea.

What we claim is:

1. An apparatus for making tomographic or normal surveys by means of a gamma camera, comprising a base frame, a discoidal member supported at its periphery vertically on said base and for rotation coaxially about its axis, an articulated support for a survey head containing a gamma camera means mounting said support on said member for movement thereon radially of said axis, the discoidal member having therein a central hole through which the body of a patient supported on a sliding bed can pass, and motor means for rotating the discoidal member and for radially moving the head support thereon.

2. An apparatus as claimed in claim 1, wherein a fork is pivoted on said support about a first horizontal axis, the survey head being pivoted to the fork about a second horizontal axis orthogonal to the first, the fork and the head being rotatable about their respective pivoting axes by further motor means.

3. An apparatus as claimed in claim 1, wherein said discoidal member is supported by rolling elements resting on its periphery and acting radially and axially to guide the rotation of said member.

4. An apparatus as claimed in claim 1, wherein said discoidal member is provided peripherally with a ring gear in which a pinion gear driven by a geared motor engages.

5. An apparatus as claimed in claim 4, wherein a worm also engages in said ring gear and is kinematically linked to the pinion by an angular speed ratio such that the peripheral advancement imposed on the ring gear by the pinion is equal to that of the worm, the engagement between the worm and ring gear being slack such as to prevent any false transmission, and the worm pitch being such as to prevent reversibility of the worm-ring gear coupling.

6. An apparatus as claimed in claim 1, wherein the frame has a pair of legs projecting horizontally therefrom and said frame and legs rest on the ground by way of telescopic feet to vary the height of the apparatus.

7. An apparatus as claimed in claim 6, wherein the feet are carried by threaded shanks which screw into nut screws fixed to the frame and legs and which rigidly carry sprocket wheels which engage in an endless chain driven by another motor means.

8. An apparatus as claimed in claim 1, wherein to said discoidal member there are fixed guides on which said support slides radially and comprising a nut screw into which is screwed a worm rotatably supported on the member and rotated by still further motor means.

9. An apparatus as claimed in claim 1, wherein a second support is mounted on the support surface for the frame, and to the rear thereof, and defines a horizontal cantilever guide which extends axially through the central hole in the discoidal member and terminates before the position corresponding to the vertical axis through the center of the survey head.

10. An apparatus as claimed in claim 9, wherein a third vertical removable support is disposed in front of the apparatus to constitute an extension to the cantilever guide, for slidably receiving the bed for a patient.

* * * * *